United States Patent
Chan et al.

(10) Patent No.: US 9,307,908 B2
(45) Date of Patent: Apr. 12, 2016

(54) MEASURING PSYCHOLOGICAL STRESS FROM CARDIOVASCULAR AND ACTIVITY SIGNALS

(71) Applicant: Vital Connect, Inc., Campbell, CA (US)

(72) Inventors: Alexander Chan, Campbell, CA (US); Ravi Narasimhan, Sunnyvale, CA (US)

(73) Assignee: VITAL CONNECT, INC., Campbell, CA (US)

( * ) Notice: Subject to any disclaimer, the term of this patent is extended or adjusted under 35 U.S.C. 154(b) by 670 days.

(21) Appl. No.: 13/664,199

(22) Filed: Oct. 30, 2012

(65) Prior Publication Data
US 2014/0121543 A1    May 1, 2014

(51) Int. Cl.
A61B 5/00 (2006.01)
A61B 5/0468 (2006.01)
A61B 5/16 (2006.01)
A61B 5/11 (2006.01)

(52) U.S. Cl.
CPC .............. *A61B 5/0006* (2013.01); *A61B 5/0468* (2013.01); *A61B 5/165* (2013.01); *A61B 5/1123* (2013.01)

(58) Field of Classification Search
None
See application file for complete search history.

(56) References Cited

U.S. PATENT DOCUMENTS

| 7,160,253 B2 | 1/2007 | Nissila |
| 7,213,600 B2 | 5/2007 | El-Nokaly et al. |
| 7,991,458 B2 | 8/2011 | Hardahl et al. |
| 2011/0061647 A1* | 3/2011 | Stahmann ............ A61B 5/0031 128/202.16 |

FOREIGN PATENT DOCUMENTS

WO   WO 2009/138923   11/2009

OTHER PUBLICATIONS

The International Search Report and the Written Opinion of the International Searching Authority issued for International Application No. PCT/US2013/058302, mailed Dec. 19, 2013.

* cited by examiner

*Primary Examiner* — Brian T Gedeon
*Assistant Examiner* — Ankit Tejani
(74) *Attorney, Agent, or Firm* — Sawyer Law Group, P.C.

(57) ABSTRACT

A method and system for measuring psychological stress disclosed. In a first aspect, the method comprises determining R-R intervals from an electrocardiogram (ECG) to calculate a standard deviation of the R-R intervals (SDNN) and determining a stress feature (SF) using the SDNN. In response to reaching a threshold, the method includes performing adaptation to update a probability mass function (PMF). The method includes determining a stress level (SL) using the SF and the updated PMF to continuously measure the psychological stress. In a second aspect, the system comprises a wireless sensor device coupled to a user via at least one electrode, wherein the wireless sensor device includes a processor and a memory device coupled to the processor, wherein the memory device stores an application which, when executed by the processor, causes the processor to carry out the steps of the method.

8 Claims, 5 Drawing Sheets

MEASURING PSYCHOLOGICAL STRESS FROM CARDIOVASCULAR AND ACTIVITY SIGNALS

FIELD OF THE INVENTION

The present invention relates to sensor devices, and more particularly, to a sensor device utilized to measure psychological stress.

BACKGROUND

Psychological stress is associated with a variety of cardiovascular diseases and quantitatively measuring stress aids in stress management. Conventionally, there are two types of psychological stress: acute stress and chronic stress. Acute stress is characterized by rapid changes in the autonomic nervous system that ready the body for "fight or flight" responses to external stimuli. Chronic stress is characterized by prolonged exposure to stressful stimuli which leads to long-term sympathetic overactivity.

Conventional methods of measuring stress calculate heart rate (HR) and heart rate variability (HRV) in the time and frequency domains. However, HR and HRV are highly variable between people. This variability issue limits the continuous monitoring and accurate measuring of a person's psychological stress levels. Therefore, there is a strong need for a cost-effective solution that overcomes the above issue by adaptively measuring individualized physiology. The present invention addresses such a need.

SUMMARY OF THE INVENTION

A method and system for measuring psychological stress are disclosed. In a first aspect, the method comprises determining R-R intervals from an electrocardiogram (ECG) to calculate a standard deviation of the R-R intervals (SDNN) and determining a stress feature (SF) using the SDNN. In response to reaching a threshold, the method includes performing adaptation to update a probability mass function (PMF). The method includes determining a stress level (SL) using the SF and the updated PMF to continuously measure the psychological stress.

In a second aspect, the system comprises a wireless sensor device coupled to a user via at least one electrode, wherein the wireless sensor device includes a processor and a memory device coupled to the processor, wherein the memory device stores an application which, when executed by the processor, causes the processor to determine R-R intervals from an electrocardiogram (ECG) to calculate a standard deviation of the R-R intervals (SDNN) and determine a stress feature (SF) using the SDNN. In response to reaching a threshold, the system further causes the processor to perform adaptation to update a probability mass function (PMF). The system further causes the processor to determine a stress level (SL) using the SF and the updated PMF to continuously measure the psychological stress.

BRIEF DESCRIPTION OF THE DRAWINGS

The accompanying figures illustrate several embodiments of the invention and, together with the description, serve to explain the principles of the invention. One of ordinary skill in the art will recognize that the particular embodiments illustrated in the figures are merely exemplary, and are not intended to limit the scope of the present invention.

DETAILED DESCRIPTION OF PREFERRED EMBODIMENTS

Figure 1:
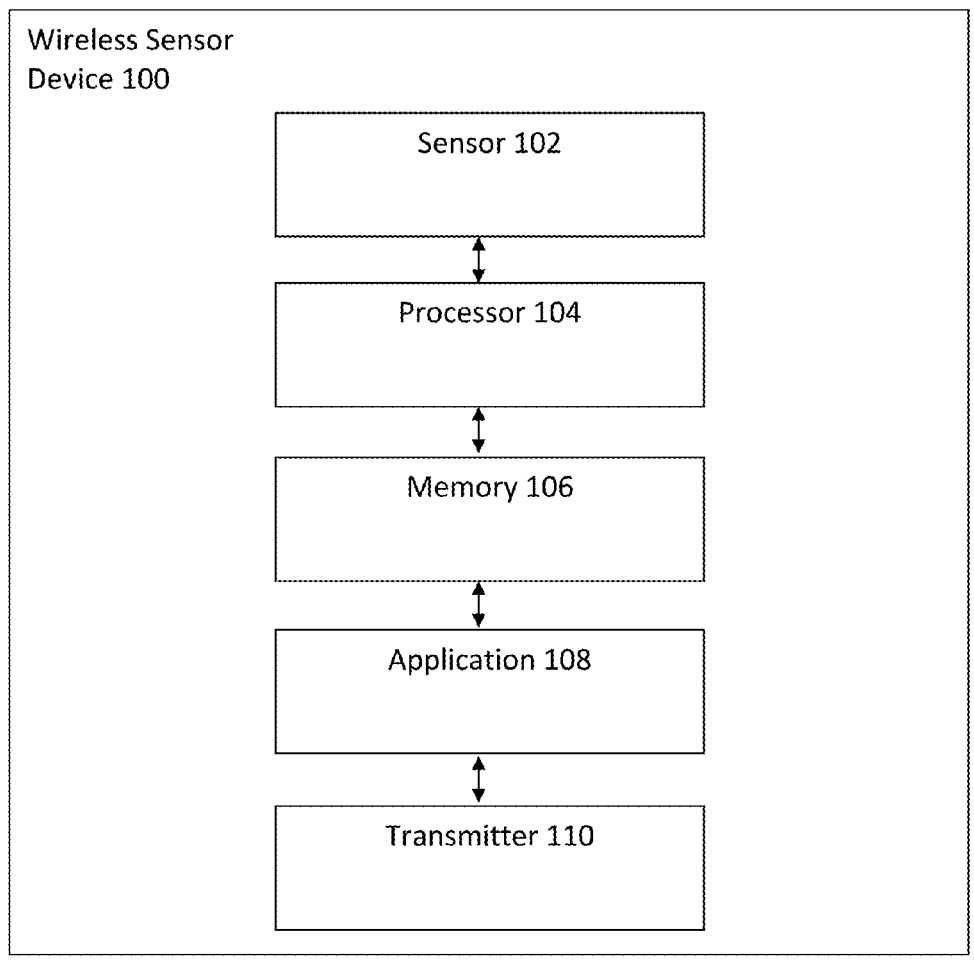
FIG. 1 illustrates a wireless sensor device in accordance with an embodiment.

The present invention relates to sensor devices, and more particularly, to a sensor device utilized to measure psychological stress. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

When left untreated, acute and chronic stress leads to a variety of health related challenges. Acute stress results in a "fight or flight" response to external stimuli. This response creates a short term increase in sympathetic tone and a decrease in parasympathetic tone. Acute stress is also characterized by an increased HR, increased low frequency HRV, decreased high frequency HRV, and a decreased galvanic skin response (GSR). Chronic stress results in long-term sympathetic overactivity. Chronic stress is also characterized by an increased baseline cortisol production, increased sympathetic activation, increased blood pressure, potentially decreased HRV, potential changes in HR, decreased physiological response to acute stress, and decreased baroreflex sensitivity.

HRV is related to the regulation of the heart by the autonomic nervous system. HRV is measured by a variety of time domain functions including but not limited to standard deviation of R-R intervals (SDNN), root-mean-square of successive R-R intervals (RMSSD), and a proportion of successive R-R intervals differing by a predetermined time period (e.g. >50 ms). An R-R interval is the interval from the peak of one QRS complex to the peak of the next as shown on an electrocardiogram. HRV is measured by a variety of frequency domain functions including but not limited to low frequency (LF) power from a predetermined range (e.g. 0.04 to 0.15 Hz), high frequency (HF) power from a predetermined range (e.g. 0.15 to 0.4 Hz), and a LF/HF ratio.

A method and system in accordance with the present invention utilizes a combination of heart rate (HR) and heart rate variability determined via the SDNN and specific posture analysis to continuously measure stress levels of an individual person. Changing postures from sitting to standing and then from standing to walking increases a person's HR and decreases the HRV.

The person's psychological stress is measured by determining R-R intervals from an electrocardiogram (ECG) to calculate a standard deviation of the R-R intervals (SDNN) and instantaneous heart rate (HR), wherein a stress feature (SF) is determined using the SDNN and HR. After a predetermined time interval, adaptation is performed to update a probability mass function (PMF) of the stress feature (SF) and a stress level (SL) is determined using the SF and the PMF to continuously measure the psychological stress. The SL determination normalizes stress measurements between a value range of 0 to 1 because individual stress features (SFs) are highly variable.

One of ordinary skill in the art readily recognizes that a variety of sensor devices can be utilized for the measuring of psychological stress including portable wireless sensor devices with embedded circuitry in a patch form factor and that would be within the spirit and scope of the present invention.

To describe the features of the present invention in more detail, refer now to the following description in conjunction with the accompanying Figures.

FIG. 1 illustrates a wireless sensor device 100 in accordance with an embodiment. The wireless sensor device 100 includes a sensor 102, a processor 104 coupled to the sensor 102, a memory 106 coupled to the processor 104, an application 108 coupled to the memory 106, and a transmitter 110 coupled to the application 108. The sensor 102 obtains data from the user and transmits the data to the memory 106 and in turn to the application 108. The processor 104 executes the application 108 to process ECG signal information of the user. The information is transmitted to the transmitter 110 and in turn relayed to another user or device.

In one embodiment, the sensor 102 comprises two electrodes to measure cardiac activity and an accelerometer to record physical activity and posture and the processor 104 comprises a microprocessor. One of ordinary skill in the art readily recognizes that a variety of devices can be utilized for the processor 104, the memory 106, the application 108, and the transmitter 110 and that would be within the spirit and scope of the present invention.

Figure 2:
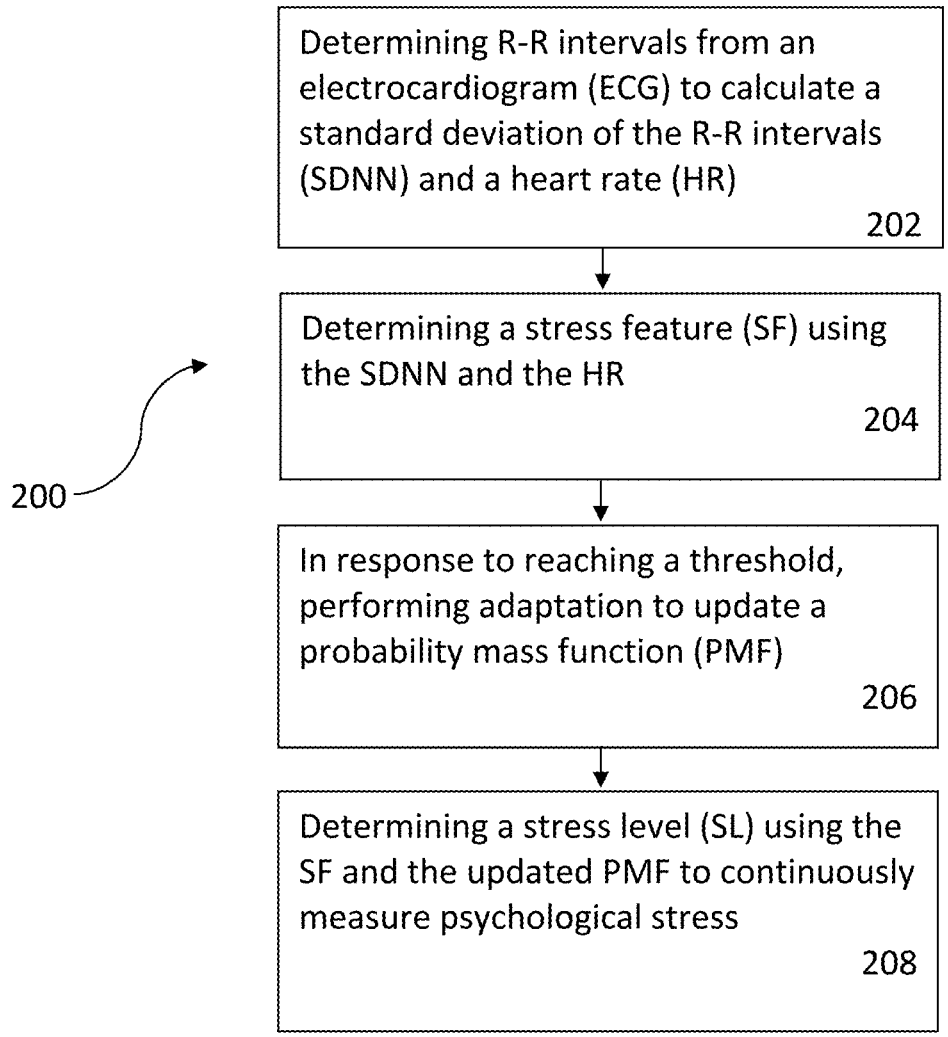
FIG. 2 illustrates a flow chart of a method for measuring psychological stress in accordance with an embodiment.

FIG. 2 illustrates a flow chart of a method 200 for measuring psychological stress in accordance with an embodiment. Referring to FIGS. 1 and 2 together, the method 200 comprises the wireless sensor device 100 determining R-R intervals from an electrocardiogram (ECG) to calculate a standard deviation of the R-R intervals (SDNN) and a heart rate (HR), via step 202, and determining a stress feature (SF) using the SDNN and the HR, via step 204. In response to reaching a threshold, the method 200 includes performing adaptation to update a probability mass function (PMF), via step 206. The method 200 includes determining a stress level (SL) using the SF and the PMF to continuously measure the psychological stress, via step 208.

In one embodiment, the method 200 further includes determining a posture state, wherein the psychological stress is not measured if the posture state is active. The posture state comprises a variety of states including but not limited to active (e.g. walking, running, etc.), siting, and standing. A separate probability mass function (PMF) is stored for each possible posture. In another embodiment, the method 200 further includes displaying the determined SL to a user or another device.

In one embodiment, determining R-R intervals from the ECG to calculate the SDNN and the HR via step 202 comprises coupling the wireless sensor device 100 via at least one electrode to measure the ECG of a user and detecting R peaks from the ECG within a predetermined time period. In this embodiment, the R-R intervals are calculated using the detected R peaks.

In one embodiment, determining a stress feature (SF) using the SDNN and the HR via step 204 comprises calculating a mean heart rate (HR) from the ECG within the predetermined time period and computing the SF utilizing an algorithm that includes the HR and the SDNN. In an embodiment, the algorithm is $SF=HR+\alpha*SDNN$, wherein $\alpha$ is predetermined negative variable that allows for combining HR and SDNN.

In another embodiment, if the wireless sensor device 100 records other relevant physiologic parameters, for example, galvanic skin response (GSR), skin temperature (TEMP), breathing rate (BR), and a square root of the mean squared difference of successive NNs (RMSSD) is utilized to compute HRV, the algorithm to compute SF is a linear combination of the parameters, for example, $SF=\alpha1*HR+\alpha2*SDNN+\alpha3*RMSSD+\alpha4*GSR+\alpha5*TEMP+\alpha6*BR$. In another embodiment, the SF is a non-linear combination of these measures, for example, the algorithm is $SF=HR^2+\alpha1*sqrt(SDNN)+\alpha2*RMSSD*GSR$ or $SF=\alpha1*HR+\alpha2*\log(SDNN)+\alpha3*TEMP^2+\alpha4*\exp(-GSR)$.

In one embodiment, performing adaptation to update the PMF via step 206 comprises grouping data into a predetermined distribution, calibrating the predetermined distribution according to a detected resting heart rate, and adjusting the predetermined distribution according to additional samples received. In an embodiment, adjusting the predetermined distribution according to additional samples received comprises multiplying all bins of the predetermined distribution by $1-\epsilon$ in response to data arriving and adding $\epsilon$ to a bin corresponding to the data.

In one embodiment, determining the stress level (SL) using the SF and the PMF via step 208 comprises adding all bins below a bin corresponding to the SF, and computing the SL utilizing an algorithm that includes a probability mass function for a given posture ($PMF_{posture}$), the SF, and the added bins. In this embodiment, the method 200 further includes adding a fraction of a current bin of the SL to improve granularity.

Long-term (e.g. weeks, months) changes in the mean and standard deviation of a stress feature probability mass function (PMF) reflects increases and/or decreases in stress. In one embodiment, the method 200 further includes tracking both a mean and a standard deviation of a probability mass function (PMF) as the PMF adapts over time and combining the mean and standard deviation to measure long-term stress.

Figure 3:
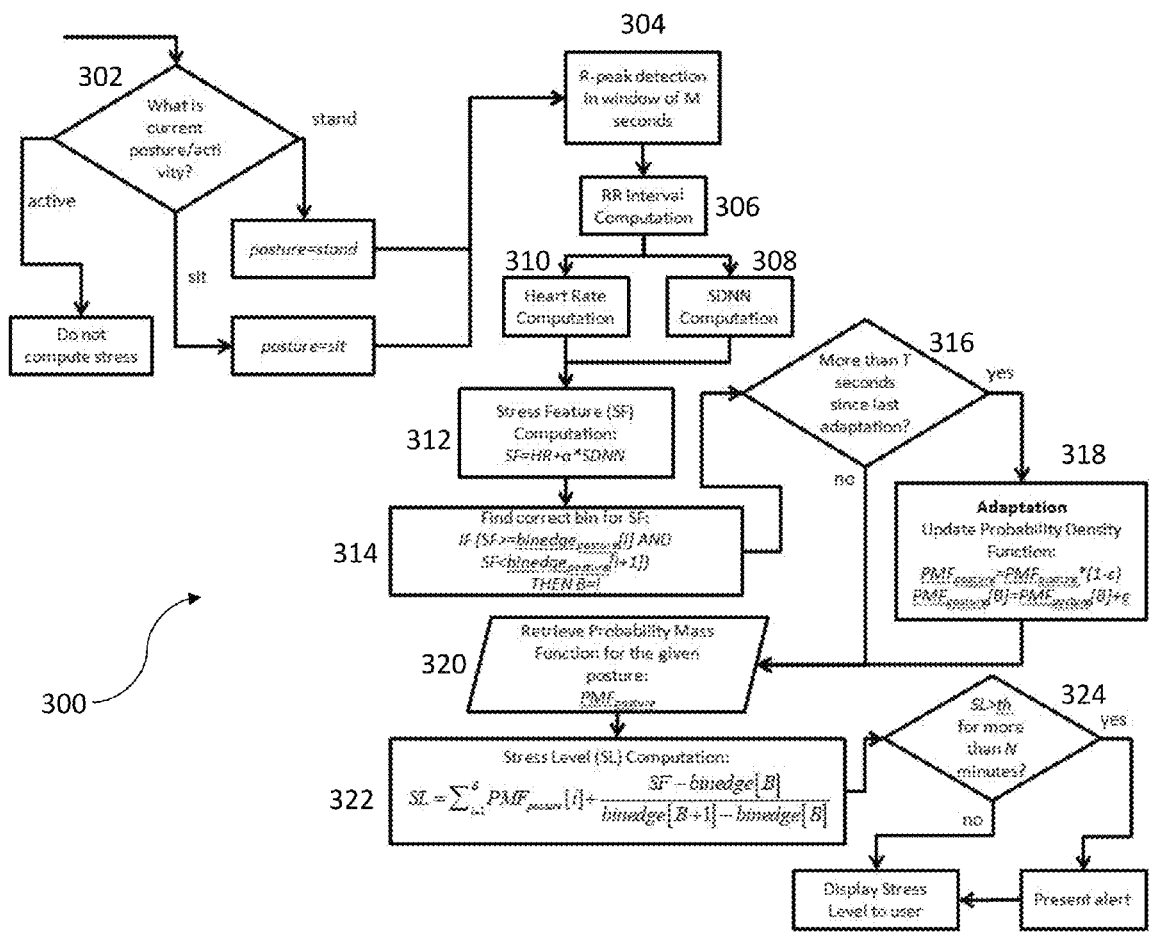
FIG. 3 illustrates a more detailed flow chart of a method for measuring psychological stress in accordance with an embodiment.

FIG. 3 illustrates a more detailed flow chart of a method 300 for measuring psychological stress in accordance with an embodiment. The method 300 includes determining the current posture/activity of a user, via step 302. If the posture/activity is "active", the method 300 does not compute a stress level. If the posture/activity is either "stand" or "sit", the method 300 computes a stress level. The method 300 detects R-peaks within a predetermined time period, via step 304, computes R-R intervals, via step 306, computes a standard deviation of R-R intervals (SDNN), via step 308, and computes a heart rate (HR), via step 310.

Utilizing these computations, the method 300 computes a stress feature (SF) per the following equation: $SF=HR+\alpha*SDNN$, via step 312. The SF is highly variable between individuals and in one embodiment, is between a predetermined range of −20 to 160. Because of this variability, a standardized stress level with a value range between 0 and 1 is computed that is relatively normalized between people. The a value is typically negative and is the weighting that allows for combining HR and SDNN and in one embodiment, $\alpha$ is defaulted as −0.315. The method 300 includes finding a correct bin for the SF per the following equation: IF ($SF>=binedge_{posture}[k]$ AND $SF<binedge_{posture}[i+1]$), THEN B=i, via step 314.

The $binedge_{posture}[i]$ includes the edges of the bins for the stress feature and the number of bins and spacing of bin edges is set depending upon desired granularity. In one embodiment, for 180 bins from −20 to 160, bin edges are set as −20, −19, −18 . . . , 159, 160). The bins are used for the PMF/histogram and B is the bin that the current SF falls into.

The method 300 determines whether more than a predetermined number of seconds (T) has passed since a last adaptation, via step 316. In one embodiment, T is defaulted as 600 seconds. If yes (more than T seconds have passed since the last adaptation), then the method 300 updates a probability mass function (PMF) via an adaptation function per the following equation: $PMF_{posture}=PMF_{posture}*(1-\epsilon)$ and $PMF_{posture}[B]=PMF_{posture}[B]+\epsilon$, where $\epsilon$ is a "forgetting" parameter for how much the PMF/histogram is changed with each adaptation run, via step 318. In one embodiment, $\epsilon$ is defaulted as 0.0003. The method 300 retrieves a probability mass function (PMF) for the given posture as $PMF_{posture}$, via step 320, which is used to calculate the stress level (SL).

The stress level (SL) measures the stress of an individual on a scale from 0 to 1, where 0 indicates no or very little stress and 1 indicates extremely high stress. The method 300 computes the SL per the following equation, via step 322:

$$SL = \sum_{i=1}^{B} PMF_{posture}[i] + SF - \frac{binedge[B]}{binedge[B+1] - binedge[B]}.$$

In this equation, all the bins below the current bin B that the SF falls into are added and a fraction of the current bin B is added to result in improved granularity. There is a separate probability mass function (PMF) for each posture because different postures have different HR and SDNN values. The method 300 determines whether the computed SL is greater than a threshold (th) for more than N minutes, via step 324. If yes, an alert is presented to the user. After the SL is computed, it is displayed via the wireless sensor device 100.

In one embodiment, the adaptive function comprises initializing, calibrating, and adapting steps. The initializing step includes beginning with a group probability mass function (PMF) that is a discretized Gaussian distribution predetermined from group training data. The calibrating step includes shifting the probability distribution according to detected resting heart rates. The adapting step includes adjusting the PMF as new samples arrive or as frequently/infrequently as desired. When new data arrives, all bins are multiplied by $1-\epsilon$ (e.g. 0.9997) and $\epsilon$ (e.g. 0.0003) is added to a bin corresponding to the new data. This adaptation adjusts the probability distribution over the course of days to weeks to fit the particular person's average distribution of stress over the course of the day.

Figure 4:
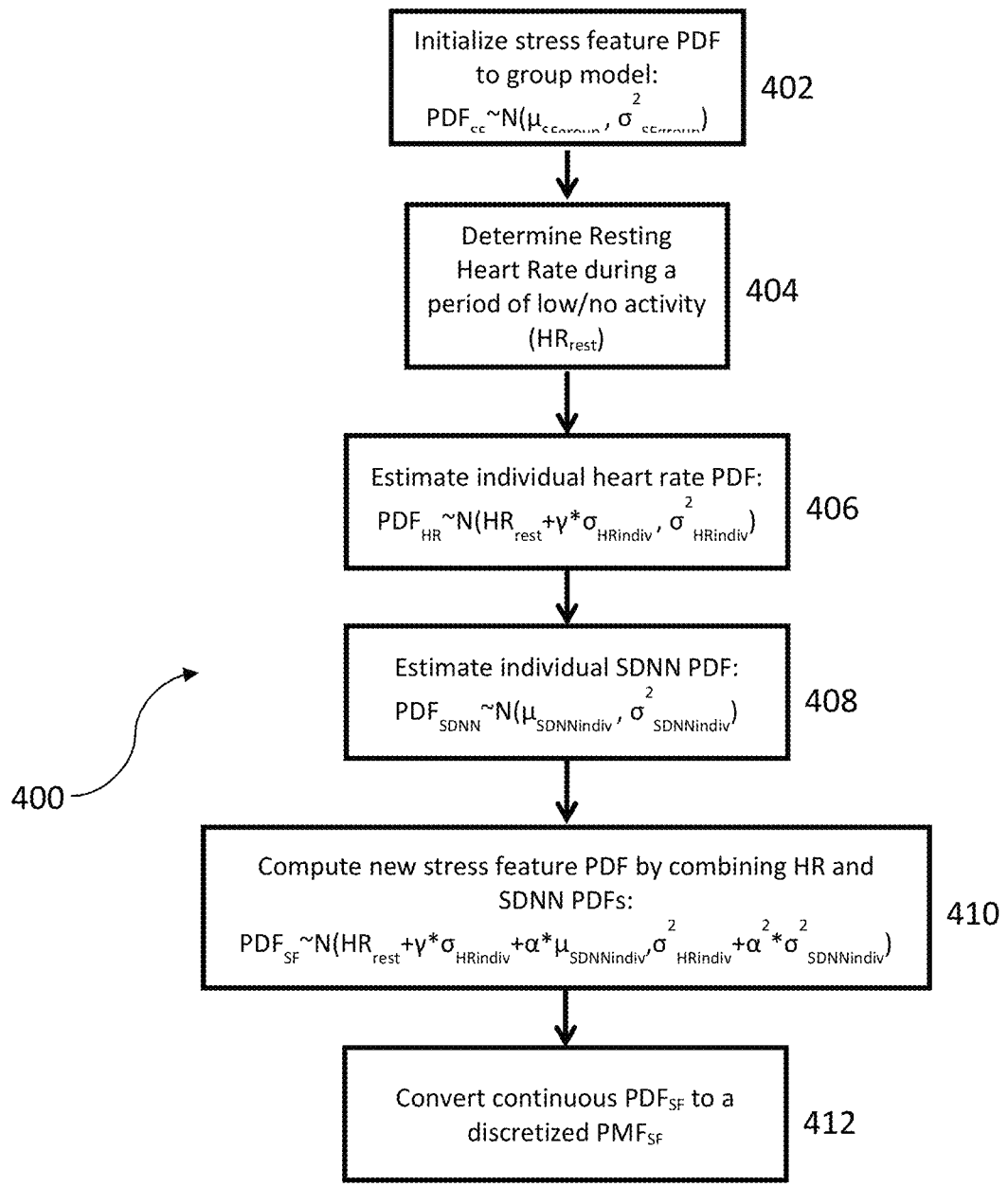
FIG. 4 illustrates a more detailed flow chart of a method for adaptive function calibration in accordance with an embodiment.

FIG. 4 illustrates a more detailed flow chart of a method 400 for adaptive function calibration in accordance with an embodiment. The method 400 includes initializing a stress feature probability density function (PDF) to a predetermined group model per the following equation: $PDF_{SF}\sim N(\mu_{SFgroup}, \sigma^2_{SFgroup})$, via step 402. The notation $N(\mu,\sigma^2)$ is a normal/Gaussian distribution with mean $\mu$ and variance $\sigma^2$ and $\mu_{SFgroup}$ and $\sigma^2_{SFgroup}$ are predetermined from the group training data.

The method 400 determines a resting heart rate ($HR_{rest}$) of a user during a period of low or no activity, via step 404. The $HR_{rest}$ is estimated from the user's data and can be during no activity or sleep periods. The method 400 estimates an individual heart rate (HR) PDF per the following equation: $PDF_{HR}\sim N(HR_{rest+rest}+\gamma*\sigma_{HRindiv}, \sigma^2_{HRindiv})$, via step 406 and estimates an individual SDNN PDF per the following equation: $PDF_{SDNN}\sim N(\mu_{SDNNindiv}, \sigma^2_{SDNNindiv})$, via step 408.

The method 400 computes a new stress feature PDF by combining the determined HR and SDNN PDFs per the following equation: $PDF_{SF}\sim N(HR_{rest}+\gamma*\sigma_{HRindiv}+\alpha*\mu_{SDNNindiv}, \sigma^2_{HRindiv}+\alpha^2 I\sigma^2_{SDNNindiv})$, via step 410. The continuous $PDF_{SF}$ is converted to a discretized probability distribution, or probability mass function ($PMF_{SF}$), via step 412. In one embodiment, the conversion is done by sampling the $PDF_{SF}$ within a predetermined interval and normalizing the sum to 1.

In one embodiment, the $\gamma$ value is a constant offset above $HR_{rest}$ for the mean of the HR distribution (e.g. $\gamma=2$). The $\sigma_{HRindiv}$, $\sigma_{SDNNindiv}$, $\mu_{SDNNindiv}$ values are predetermined and fixed and are computed from the group training data. The $\sigma_{HRindiv}$ and $\sigma_{SDNNindiv}$ values are computed as the mean of the individual standard deviations in the group training data and the $\mu_{SDNNindiv}$ value is computed as the mean of the mean SDNN of all individuals in the group training data.

Long-term changes in the mean and standard deviation of the stress feature PMF reflect increases or decreases in stress. Increased chronic stress is seen in an upwards long-term shift of the SF probability distribution and increased chronic stress also decreases the response to acute stress, resulting in a narrow SF probability distribution or a smaller standard deviation.

In one embodiment, tracking the mean and the standard deviation of this SF probability distribution as it adapts over time and combining these results enables a measure of long-term stress per the following equation: $SF_{long}=\mu_{SF}-\beta*\sigma_{SF}$, where $\mu_{SF}$ is the mean of the SF from the current probability distribution $$\left(\mu_{SF} = \sum_{i} SF_i * PMF[SF_i]\right),$$

$\sigma_{SF}$ is the standard deviation of the SF from the current probability distribution $$\left(\sigma^2_{SF} = \sum_{i} (SF_i - \mu_{SF})^2 * PMF[SF_i]\right),$$

and B is a positive value.

If a person's mean stress feature probability mass function/probability distribution ($PMF_{SF}$) increases over time, $\mu_{SF}$ will increase and $SF_{long}$ will increase. If a person becomes less responsive to acute stress due to chronic stress, the standard deviation of the SF distribution will decrease because they are not responding to different increases/decreases in acute stress, resulting in the $\sigma_{SF}$ decreasing and the $SF_{long}$ once again increasing. In one embodiment, $SF_{long}$ is computed from the current $PMF_{SF}$ at various time periods including but not limited to once every few days and tracked over various time periods including but not limited to weeks and months.

In one embodiment, to determine the group training data, users are subjected to alternating blocks of relaxation and stress. The blocks ranged from 3 to 7 minutes in length, relaxation involved various acts including but not limited to sitting quietly or listening to classical music, and stress involved various acts including but not limited to watching a movie clip from an active/horror movie, playing tetris, performing a stroop test, performing a series of mental arithmetic problems, and playing a competitive online real-time strategy game.

Figure 5:
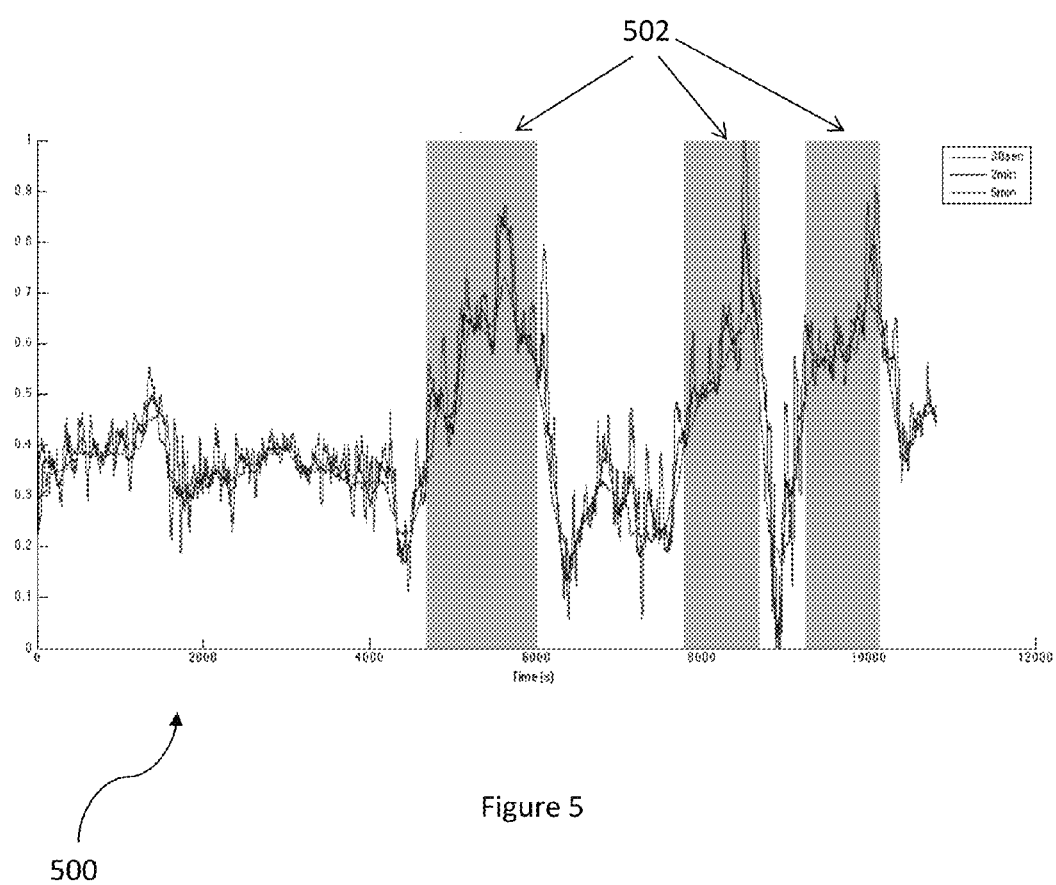
FIG. 5 illustrates a diagram of stress level computation in accordance with an embodiment.

FIG. 5 illustrates a diagram 500 of stress level computation in accordance with an embodiment. In the diagram 500, the y axis represents the stress level from 0 to 1 and the x axis represents time. A predetermined window of time for computing the stress level is variable depending on the necessary time resolution and the application (e.g. gaming versus daily use). Shorter windows allow changes in stress to be detected much faster but include additional noise. During periods of stress 502, such as playing a game, the stress level increases to values closer to 1.

Additionally, while the probability mass function (PMF) is adapted for each person, the best stress feature or the best combination of HR and SDNN is learnable for each person. In one embodiment, individual learning is done via supervised learning including but not limited to Fisher Discriminants that learn the best $\alpha$, which is the weighting parameter for combining HR and SDNN for each person.

In an embodiment, a semi-supervised approached is utilized to learn the best feature including but not limited to self-training where an individual performs a few minutes of a relaxation activity (e.g. metronome breathing) and a few minutes of a stressful activity (e.g. playing tetris). The two data points are used to determine an initial projection line defined by the $\alpha$ parameter and new data is classified and the most confident data points are used by the wireless sensor device 100 to continuously and automatically adjust the $\alpha$ parameter.

As above described, the method and system allow for measuring psychological stress of a user of a wireless sensor device. By determining current posture, detecting R-peaks from an ECG within a predetermined window of time to compute mean heart rate (HR) and SDNN, combining the HR and the SDNN to calculate a stress feature (SF) that is highly variable between different people, determining a current bin that the SF falls into within a predetermined bin range, and determining a latest probability mass function (PMF) and summing all bins of the PMF below the current bin, a cost-effective and continuous stress level (SL) measurement system is achieved.

The predetermined window of time includes but is not limited to 120 seconds and the predetermined bin range includes but is not limited to −20 to 160 with a width of 1. If a threshold time period has passed since last adaptation, the method and system perform adaptation of the probability mass function (PMF)/probability distribution using the current SF. The current stress level (SL) of the user is either displayed to the user via the wireless sensor device and/or triggers a warning alert if the SL is above a threshold (th) longer than a predetermined time period of N minutes.

A method and system for measuring psychological stress has been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or computer-readable medium. The software application provides instructions that enable the processor to cause the receiver to perform the functions described herein.

Furthermore, embodiments may take the form of a computer program product accessible from a computer-usable or computer-readable storage medium providing program code or program instructions for use by or in connection with a computer or any instruction execution system. For the purposes of this description, a computer-usable or computer-readable storage medium can be any apparatus that can contain, store, communicate, propagate, or transport the program for use by or in connection with the instruction execution system, apparatus, or device.

The computer-readable storage medium may be an electronic, magnetic, optical, electromagnetic, infrared, semiconductor system (or apparatus or device), or a propagation medium. Examples of a computer-readable storage medium include a semiconductor or solid state memory, magnetic tape, a removable computer diskette, a random access memory (RAM), a read-only memory (ROM), a rigid magnetic disk, and an optical disk. Current examples of optical disks include DVD, compact disk-read-only memory (CD-ROM), and compact disk—read/write (CD-R/W).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A system for measuring psychological stress, the system comprising:
    a wireless sensor device coupled to a user via at least one electrode, wherein the wireless sensor device includes a processor; and
    a memory device coupled to the processor, wherein the memory device stores an application which, when executed by the processor, causes the processor to:
    determine R-R intervals from an electrocardiogram (ECG) to calculate a standard deviation of the R-R intervals (SDNN);
    determine a stress feature (SF) using the SDNN by calculating a mean heart rate (HR) from the ECG within a predetermined time period and by utilizing an algorithm SF =HR+$\alpha$*SDNN, wherein $\alpha$ is a predetermined negative variable that allows for combining HR and SDNN;
    in response to reaching a threshold, perform adaptation to update a probability mass function (PMF); and
    determine a stress level (SL) using the SF and the updated PMF to measure the psychological stress.

2. The system of claim 1, wherein the application further causes the processor to:
    determine a posture state, wherein the psychological stress is not measured if the posture state is active; and
    display the determined SL to a user or another device.

3. The system of claim 2, wherein the posture state includes any of active, sitting, and standing.

4. The system of claim 1, wherein to determine R-R intervals from the ECG to calculate the SDNN further comprises to:
    detect R peaks from a measured ECG within the predetermined time period; and
    calculate R-R intervals using the detected R peaks.

5. The system of claim 1, wherein to perform adaptation to update the PMF further comprises to:
    group data into a predetermined distribution;
    calibrate the predetermined distribution according to a detected resting heart rate; and
    adjust the predetermined distribution according to additional samples received.

6. The system of claim 5, wherein to adjust the predetermined distribution according to additional samples received further comprises to:
    in response to data arriving, multiply all bins of the predetermined distribution by 1-$\epsilon$; and add $\epsilon$ to a bin corresponding to the data, wherein $\epsilon$ is a parameter for how much the PMF is changed with each adaptation.

7. The system of claim 5, wherein to determine the stress level (SL) using the SF and the PMF further comprises to:
   add all bins below a bin corresponding to the SF; and
   compute the SL utilizing an algorithm that includes a probability mass function for a given posture ($PMF_{posture}$), the SF, and the added bins.

8. The system of claim 7, wherein the application further causes the processor to:
   add a fraction of a current bin to improve granularity.

* * * * *